United States Patent
De Rezende Neto

(10) Patent No.: US 11,553,905 B2
(45) Date of Patent: Jan. 17, 2023

(54) CARDIAC INJURY DEVICE

(71) Applicant: João Baptista De Rezende Neto, Toronto (CA)

(72) Inventor: João Baptista De Rezende Neto, Toronto (CA)

(73) Assignee: UNITY HEALTH TORONTO, Toronto (CA)

( * ) Notice: Subject to any disclaimer, the term of this patent is extended or adjusted under 35 U.S.C. 154(b) by 418 days.

(21) Appl. No.: 16/845,191

(22) Filed: Apr. 10, 2020

(65) Prior Publication Data

US 2020/0237354 A1 Jul. 30, 2020

Related U.S. Application Data

(60) Division of application No. 15/839,090, filed on Dec. 12, 2017, now Pat. No. 10,653,402, which is a
(Continued)

(51) Int. Cl.
*A61B 17/00* (2006.01)
*A61M 5/14* (2006.01)
*A61M 25/00* (2006.01)

(52) U.S. Cl.
CPC ........... *A61B 17/0057* (2013.01); *A61M 5/14* (2013.01); *A61M 25/0074* (2013.01);
(Continued)

(58) Field of Classification Search
CPC ...... A61B 17/0057; A61B 2017/00575; A61B 2017/00243; A61B 2017/00592;
(Continued)

(56) References Cited

U.S. PATENT DOCUMENTS 5,593,422 A 1/1997 Muijs Van de Moer et al.
7,771,455 B2 * 8/2010 Ken ................... A61B 17/0057
606/213
(Continued)

FOREIGN PATENT DOCUMENTS

EP 1891902 A1 2/2008
WO 2003094740 A1 11/2003
(Continued)

OTHER PUBLICATIONS

Aortic Reconstruction With Bovine Pericardial Grafts, Silveira et al., Rev Bras Cir Cardiovasc 2003; 18(1):9-14.
(Continued)

*Primary Examiner* — Julian W Woo
(74) *Attorney, Agent, or Firm* — ABM Intellectual Property Inc.; Adrienne Bieber McNeil

(57) ABSTRACT

A device, method, and use of a device for temporary management of a wound, such as a wound in a heart. The device has a shaft, a blood flow blocking membrane at the first end of the shaft for blocking blood flow through the wound, and an abutment member that is mounted to the shaft and is axially movable along the shaft towards and away from the blood flow blocking membrane for abutting the wound and holding the blood flow blocking membrane adjacent the wound. The blood flow blocking membrane is resiliently flexible and movable between at least a first collapsed state for inserting the blood flow blocking membrane through the wound, and a deployed state for blocking blood flow through the wound.

10 Claims, 12 Drawing Sheets

Related U.S. Application Data continuation-in-part of application No. PCT/IB2016/053827, filed on Jun. 27, 2016.

(60) Provisional application No. 62/186,472, filed on Jun. 30, 2015.

(52) U.S. Cl.
CPC ............ *A61B 2017/00243* (2013.01); *A61B 2017/00575* (2013.01); *A61B 2017/00592* (2013.01); *A61B 2017/00597* (2013.01); *A61B 2017/00606* (2013.01); *A61B 2017/00615* (2013.01); *A61B 2017/00637* (2013.01); *A61M 2230/04* (2013.01); *A61M 2230/30* (2013.01)

(58) Field of Classification Search
CPC .......... A61B 2017/00597; A61B 2017/00615; A61B 2017/00606; A61B 2017/00637; A61M 5/14; A61M 25/0074; A61M 2230/04; A61M 2230/30
See application file for complete search history.

(56) References Cited

U.S. PATENT DOCUMENTS

| | | | |
|---|---|---|---|
| 8,398,676 B2 | 3/2013 | Roorda et al. | |
| 8,506,525 B2 | 8/2013 | Bosarge | |
| 8,591,538 B2 | 11/2013 | Gellman | |
| 8,845,682 B2 | 9/2014 | Penner et al. | |
| 9,241,696 B2 | 1/2016 | Mehl | |
| 9,414,824 B2 | 8/2016 | Fortson et al. | |
| 9,883,857 B2 | 2/2018 | Shluzas et al. | |
| 2004/0254594 A1 | 12/2004 | Alfaro | |
| 2007/0179527 A1 | 8/2007 | Eskuri et al. | |
| 2008/0091235 A1 | 4/2008 | Sirota | |
| 2008/0243182 A1* | 10/2008 | Bates .................. | A61B 17/0057 606/213 |
| 2010/0185233 A1 | 7/2010 | Thommen | |
| 2010/0185234 A1* | 7/2010 | Fortson .............. | A61B 17/0057 606/213 |
| 2013/0018302 A1 | 1/2013 | Nour et al. | |
| 2014/0350588 A1 | 11/2014 | Fabian et al. | |
| 2015/0119929 A1* | 4/2015 | Penner ............... | A61B 17/0625 606/213 |
| 2018/0098760 A1 | 4/2018 | de Rezende Neto | |

FOREIGN PATENT DOCUMENTS

| | | |
|---|---|---|
| WO | 2011089459 A1 | 7/2011 |
| WO | 2012003317 A1 | 1/2012 |
| WO | 2014018907 A1 | 1/2014 |

OTHER PUBLICATIONS

Biomechanics and Biocompatibility of the Perfect Conduit—Can We Build One?, Byrom et al., Ann Cardiothorac Surg 2013;2(4):435-443.

Communication Under Rule 71 (3) EPC issued by European Patent Office dated Nov. 11, 2019 for European Patent Application No. 16817341.7.

* cited by examiner

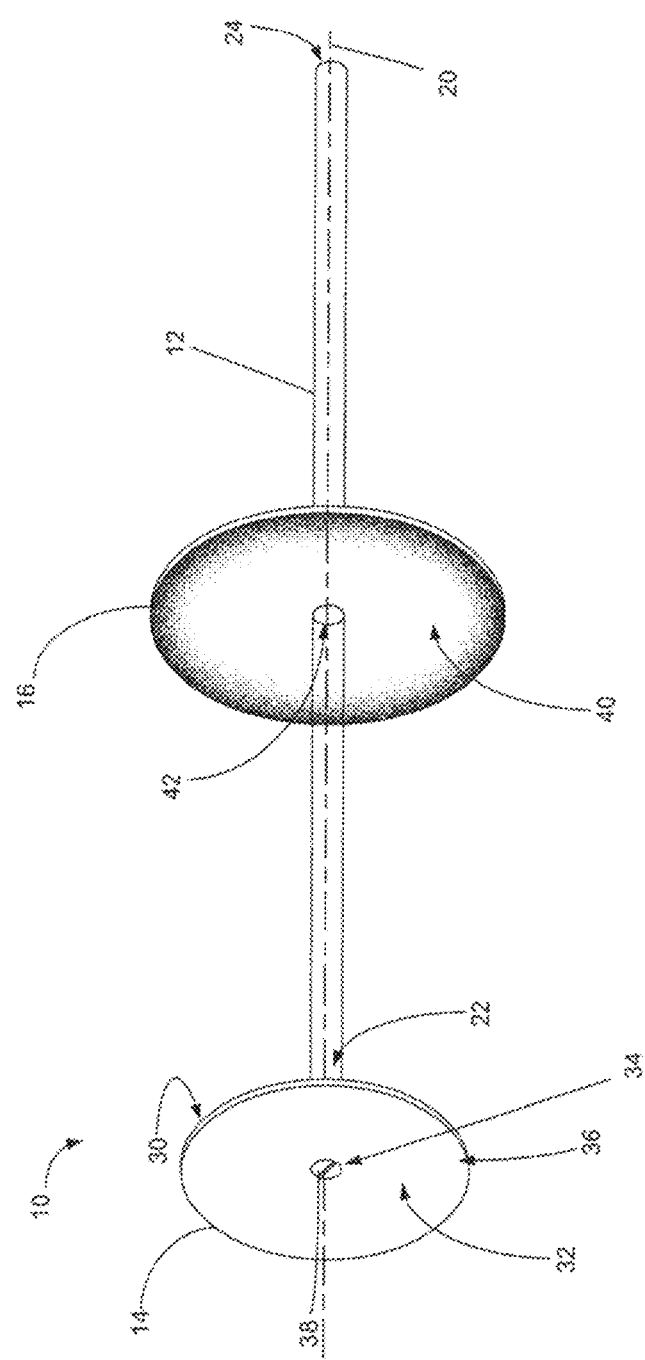

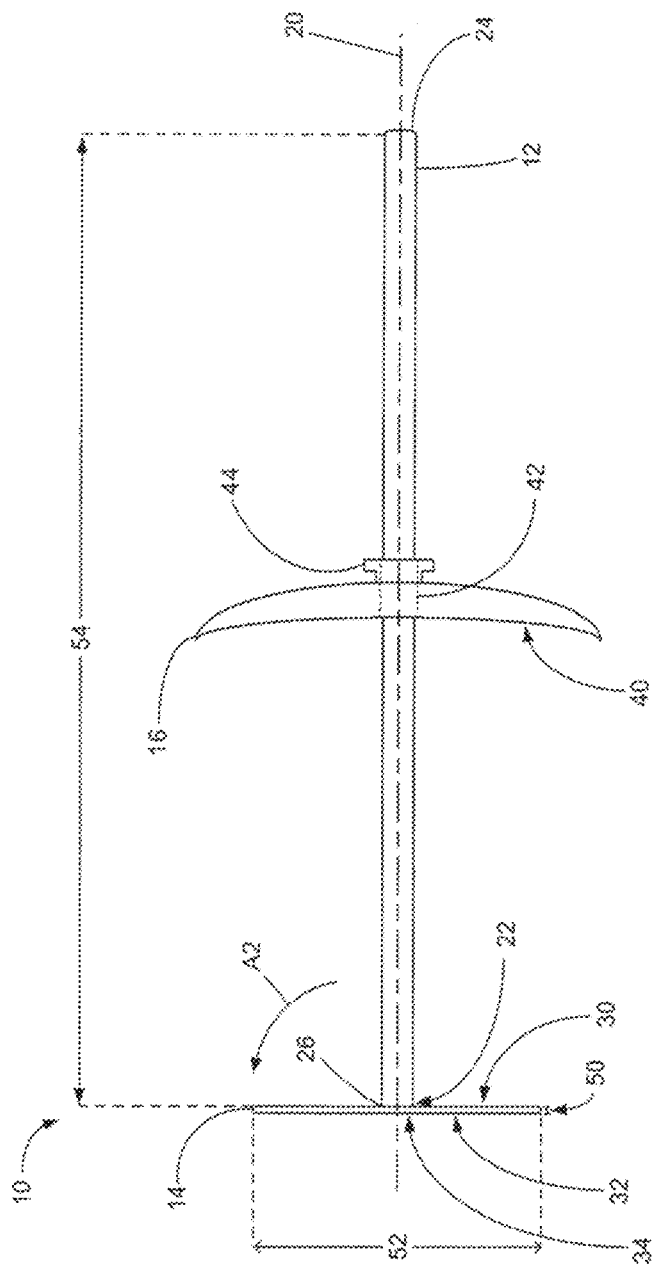

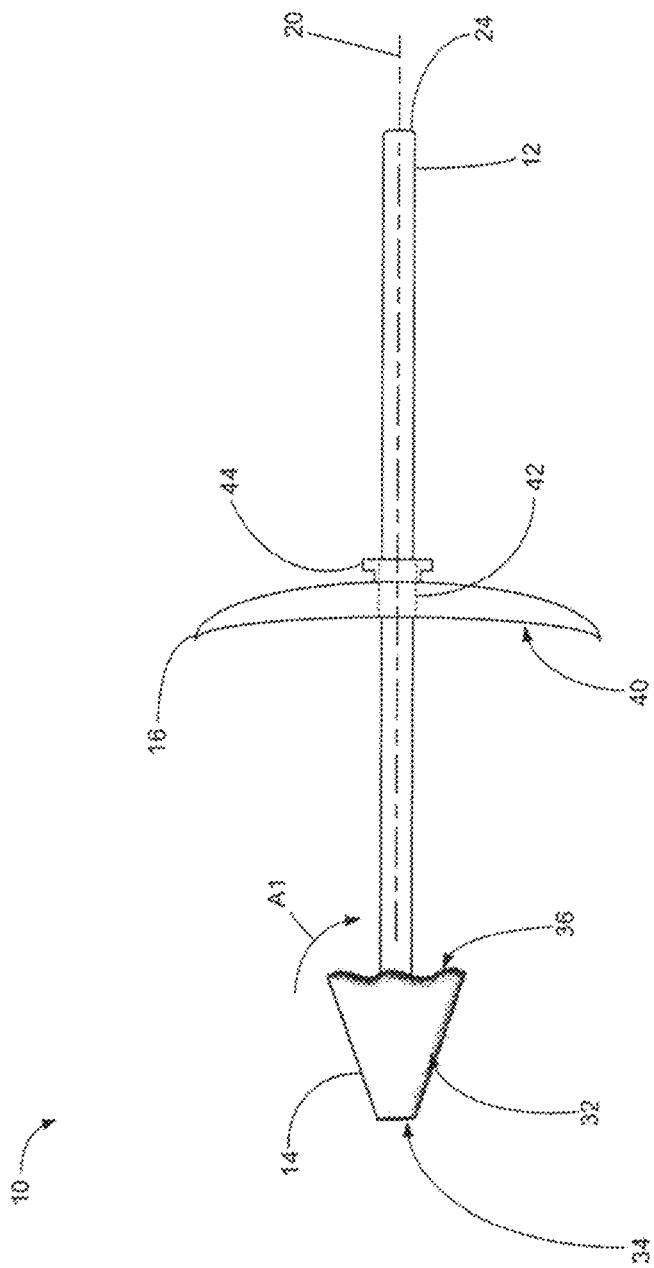

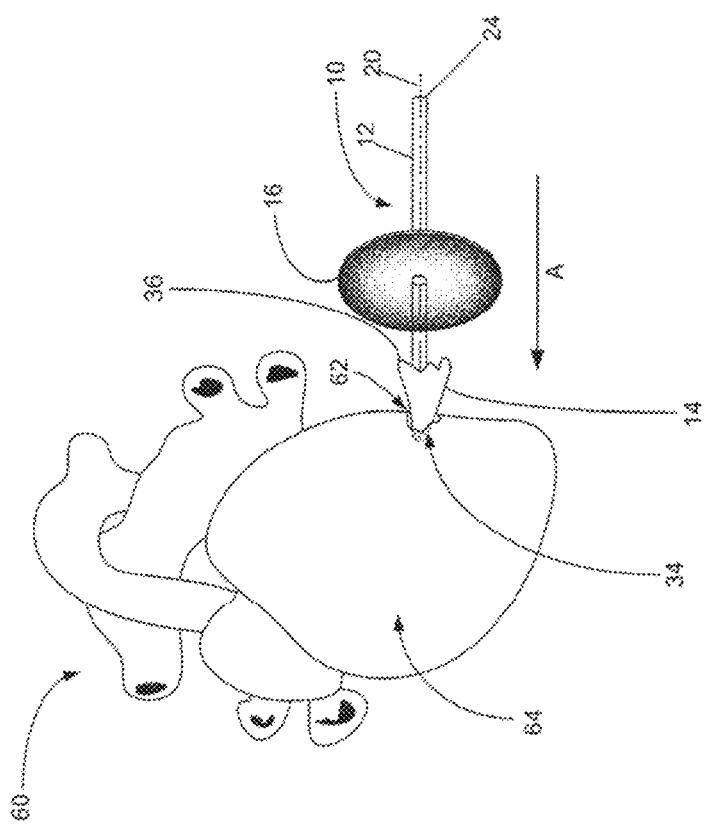

CARDIAC INJURY DEVICE

CROSS-REFERENCES TO RELATED APPLICATIONS

This application is divisional of U.S. patent application Ser. No. 15/839,090 filed on Dec. 12, 2017, which is a continuation-in-part of international patent application no. PCT/162016/053827 filed on Jun. 27, 2016, which claims the benefit of U.S. provisional patent application No. 62/186,472 filed on Jun. 30, 2015, all of which are incorporated herein by reference in their entirety.

FIELD

The disclosure relates to cardiac wound management. More specifically the disclosure relates to a device and method for temporary management of a wound in a heart.

BACKGROUND

U.S. Pat. Pub'n. No. 2013/0018302 (A1) (Nour et al.) purports to disclose a single-use device, intended to be used in surgery each time a vascular approach by cannulation or catheterization is found to be necessary, in particular in heart surgery or interventional cardiology. This device essentially includes a body, a sealing system consisting of two inflatable disks, a control connector for inflating and deflating the disk, a tubular unit and a flexible guide.

U.S. Pat. No. 8,506,525 (B2) (Bosarge) purports to disclose a wound sealing fluid delivery apparatus and method including a surface seal. A catheter with a first end and a second end is provided such that the catheter passes through the surface seal. An infusion port is connected with the first end of the catheter and an expandable internal seal is connected with the catheter at the second end.

SUMMARY

The following summary is intended to introduce the reader to various aspects of the applicant's teaching, but not to define any invention.

According to some aspects, a device for temporary management of a wound, such as a wound in a heart, includes a shaft that has a first end portion, a second end portion, and a shaft axis extending therebetween. A blood flow blocking membrane is at the first end portion for blocking blood flow through the wound. The blood flow blocking membrane has a first face facing towards the second end portion, an opposed second face facing away from the second end portion, a central portion adjacent the shaft, and a peripheral portion. The blood flow blocking membrane is resiliently flexible and movable between at least a first collapsed state in which the membrane is flexed to move the peripheral portion axially towards the second end portion and radially inwardly towards the shaft axis for inserting the blood flow blocking membrane through the wound, and a deployed state in which, relative to the first collapsed state, the peripheral portion is moved away from the second end portion and radially outwardly for blocking blood flow through the wound. The device also includes an abutment member that is mounted to the shaft and is axially movable along the shaft towards and away from the blood flow blocking membrane for abutting the wound and holding the blood flow blocking membrane adjacent the wound.

In some examples, the blood flow blocking membrane can be biased towards the deployed state.

In some examples, the blood flow blocking membrane can be fabricated from silicone.

In some examples, the blood flow blocking membrane can include a single ply silicone disc.

In some examples, the blood flow blocking membrane can be fabricated from bovine pericardium.

In some examples, at least a portion of the blood flow blocking membrane is separable from the shaft.

In some examples, the blood flow blocking membrane can be secured to the shaft in a fixed position.

In some examples, the blood flow blocking membrane can be further movable to and from a second collapsed state in which, relative to the deployed state, the membrane is flexed to move the peripheral portion axially away from the second end portion and radially inwardly towards the shaft axis for removing the blood flow blocking membrane from the wound.

In some examples, the blood flow blocking membrane can have a membrane stiffness, and the abutment member can have an abutment member stiffness greater than the membrane stiffness.

In some examples, the abutment member can be resiliently flexible.

In some examples, the abutment member can have a concave side facing towards the first end portion.

In some examples, the abutment member can have a central bore extending axially therethrough, the shaft can be received in the bore, and the abutment member can be axially slidable along the shaft.

In some examples, the shaft can extend perpendicularly from the membrane second surface.

In some examples, the shaft can have a first end at the first end portion, and the membrane can be secured to the first end. In some examples, the central portion of the membrane can be secured to the first end.

In some examples, the membrane can have a wall thickness of between about 0.25 mm and about 1.5 mm.

In some examples, the shaft can have a shaft length of between about 10 cm and about 20 cm. In some examples, the shaft can have a shaft length of 15 cm.

In some examples, the blood flow blocking membrane can have a deployed surface area and the deployed surface area can be less than 80 $cm^2$.

In some examples, the blood flow blocking membrane can have a deployed volume, and the deployed volume can be less than 6 $cm^3$.

According to some aspects, the device may be used to temporarily manage a wound in a heart.

According to some aspects, a method for temporary management of a wound, such as a wound in a heart, includes a) inserting a blood flow blocking membrane through the wound. The blood flow blocking membrane flexes to a first collapsed state as the blood flow blocking membrane passes through the wound, and returns to a deployed state when it has passed through the wound. The method also includes b) positioning the blood flow blocking membrane against the wound, such as against a wall of the heart, to cover the wound and to block blood flow through the wound. The method further includes c) maintaining the blood flow blocking membrane against the wound.

In some examples, the blood flow blocking membrane can take up no more than about 1% of the volume of the heart when in the deployed state.

In some examples, the step of inserting the blood flow blocking membrane can include inserting a first end portion of a shaft into the wound, where the blood flow blocking membrane is at the first end portion of the shaft.

In some examples, the step of positioning the blood flow blocking membrane can include retracting the shaft to position the blood flow blocking membrane against the wound, such as against the wall of the heart.

In some examples, the step of maintaining the blood flow blocking membrane against the wound can include moving an abutment member axially along the shaft towards the wound, such as towards the heart to contact the heart.

In some examples, in the step of inserting the blood flow blocking membrane through the wound can cause the blood flow blocking membrane to flex to the collapsed state In some examples, in the step of inserting the blood flow blocking membrane, the blood flow blocking membrane can automatically return to the deployed state after passing through the wound.

In some examples, the method can further include applying a stitch to the wound while the blood flow blocking membrane is in the heart, for example when it is in the deployed state in the heart.

In some examples, the method can further include retracting the blood flow blocking membrane from the wound. The blood flow blocking membrane can flex to a second collapsed state as the blood flow blocking membrane passes through the wound.

In some examples, the method can further include applying a stitch to the wound to stitch a portion of the blood flow blocking membrane to the wound, and separating the portion of the blood flow blocking membrane from the shaft. The method can further include retracting the shaft and the abutment member from the wound.

BRIEF DESCRIPTION OF THE DRAWINGS

The drawings included herewith are for illustrating various examples of articles, methods, and apparatuses of the present specification and are not intended to limit the scope of what is taught in any way. In the drawings:

FIG. 1A is a perspective view of an example device for temporary management of a wound with a blood flow blocking membrane in a deployed state;

FIG. 1B is a top view of the example device of FIG. 1 with the blood flow blocking membrane in a deployed state;

FIG. 1C is a top view of the example device of FIG. 1 with the blood flow blocking membrane in a first collapsed state;

FIG. 2B shows the example device of FIG. 1 being inserted into the wound of FIG. 2A with the blood flow blocking membrane in the first collapsed state;

DETAILED DESCRIPTION

Figure 2A:
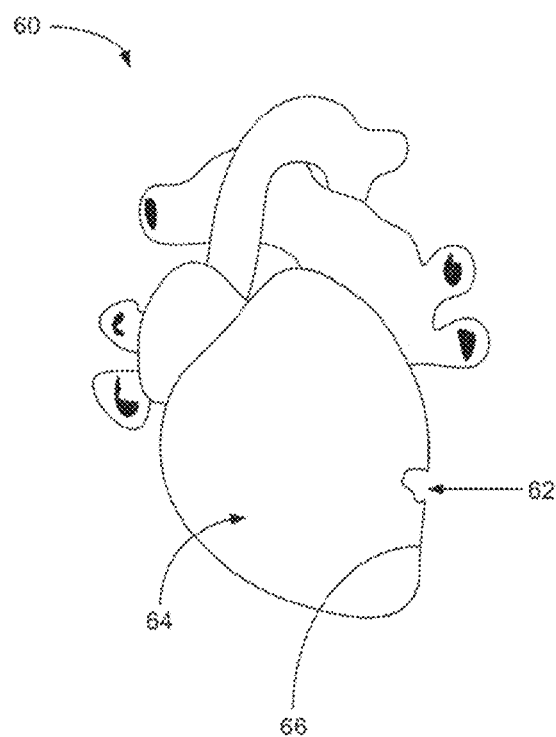
FIG. 2A is an example of a heart with a wound.

Various apparatuses or processes will be described below to provide an example of an embodiment of the claimed subject matter. No embodiment described below limits any claim and any claim may cover processes or apparatuses that differ from those described below. The claims are not limited to apparatuses or processes having all of the features of any one apparatus or process described below or to features common to multiple or all of the apparatuses described below. It is possible that an apparatus or process described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Described herein are devices and methods, and uses thereof, for temporarily managing a wound, such as a wound in a heart. As used herein, the term "wound in a heart" refers to any type of wound in a heart, including but not limited to lacerations, incisions, and/or perforations that may occur in a patient's heart. The term "wound in a heart" can be used to refer to intentional wounds or lacerations or incisions or perforations created by doctors or surgeons, such as incisions for introducing a catheter to the heart. The term "wound in a heart" can also be used to refer to unintentional wounds or lacerations or incisions or perforations howsoever caused in a patient's heart. Such wounds may include stab wounds or gunshot wounds. Penetrating cardiac wounds carry a high mortality rate. Expeditious hemorrhage control can be key to survival. In other examples, the devices and methods described herein can be used for temporary management of wounds in other body parts, such as vascular wounds, whether intentional, unintentional, or naturally occurring (e.g. in the case of aneurysms).

The devices and methods described herein can be used in various situations where bleeding from a wound, such as a wound in a heart, needs to be controlled temporarily. For instance, a cardiac surgeon may create an incision in a patient's heart to introduce a catheter. Typically, the surgeon would have to temporarily suture the incision until the procedure being performed is completed. The devices and methods described herein may provide alternatives for temporarily controlling the wound and blocking bleeding from the wound while the procedure is performed. Once the procedure is completed, the device (in whole or in part) can be removed and the wound can be sutured closed.

In some examples described herein, the device can be sized to allow some initial sutures to be applied to the wound prior to removing the device from the wound (e.g. from the heart). This may reduce the size of the wound and thereby reduce the bleeding that occurs while a medical professional finalizes the sutures to close the wound.

The devices and methods described herein can be used with various other procedures in which a wound or incision is made in a heart. For example, percutaneous aortic valve replacement, also known as transcatheter aortic valve implantation or transcatheter aortic valve replacement may involve incisions in a heart. The devices and methods described herein can be used in such procedures to temporarily stop bleeding that may occur in the wound created in the heart to replace the aortic value.

The devices and methods described herein may also be applied to traumatic or unintentional wounds in a heart. For example, if a patient is admitted with a traumatic wound that penetrates the heart the devices and methods described herein may be used to rapidly and temporarily stop or block or halt the bleeding from the wound in the heart. For example, emergency room personnel may use the device to minimize blood loss before a patient is transferred to an operating room. As well, the devices and methods described herein may be applied to stanch the bleeding from wounds unintentionally/accidentally made in a patient's heart during surgery.

As mentioned above, the devices and methods described herein may also be applied to vascular wounds, including aneurysms.

Referring to FIGS. 1A to 1C, shown therein are examples of a device 10 for temporary management of a wound, such as a wound in a heart. Device 10 can be used to cover a wound and block or halt the flow of blood through the wound. The example device 10 illustrated includes a shaft 12, a blood flow blocking membrane 14 and an abutment member 16.

Generally, in some examples, membrane 14 can be positioned inside the heart against a wall of the heart to cover the wound and block blood flow through the wound. Abutment member 16 can be used to maintain membrane 14 against the wound by contacting the outside of the wall of the heart, and preventing the device 10 from being drawn into the heart.

Shaft 12 has a first end portion 22, a second end portion 24 and a shaft axis 20 extending therebetween. Shaft 12 has a first end 26 at the first end portion 22. Shaft 12 supports membrane 14 and abutment member 16. When device 10 is used to block blood flow from a wound in a heart, the second end portion 24 of the shaft 12 may be grasped by a doctor or other medical professional to maneuver device 10 into the desired position.

In some examples, shaft 12 can have a shaft length 54 of between about 10 cm and about 20 cm. For example, shaft 12 may have a shaft length 54 of 15 cm. This may provide suitable length for the shaft 12 to extend out of a patient's body when device 10 is inserted into a wound in the patient's heart.

In some examples, shaft 12 can include or define a conduit (e.g. shaft 12 can be hollow), to allow for infusion of fluids directly into the heart. In other examples, shaft 12 may be solid or partially solid.

Blood flow blocking membrane 14 (also referred to as membrane 14) can be used for blocking blood flow through the wound in a patient's heart. Membrane 14 can be positioned against a wall of the heart to cover the wound from the interior of the heart chamber and block blood flow through the wound.

Membrane 14 is positioned at the first end portion 22 of shaft 12. Membrane 14 has a first face 30 facing towards the second end portion 24 of shaft 12 and an opposed second face 32 facing away from the second end portion 24. In the example of FIG. 1, shaft 12 extends generally perpendicularly from membrane second face 32. Membrane 14 has a central portion 34 adjacent shaft 12 and a peripheral portion 36.

In the example shown in FIG. 1A, membrane 14 is secured to shaft 12 at the first end 26. In particular, the central portion 34 of membrane 14 is secured to the first end 26. Having membrane 14 secured at the first end 26 of shaft 12 may minimize the penetration depth of the shaft 12 when membrane is positioned against the wall of the heart and covering the wound. This may minimize the volume of the heart occupied by device 10 when in use. In some examples, the blood flow blocking membrane can be secured to the shaft in a fixed position.

In the example shown, a membrane attachment 38 in the form of a screw is used to secure the membrane 14 to the shaft 12. In other examples, alternative membrane attachments, such as adhesives, can be used to secure membrane 14 to shaft 12. In other examples, membrane 14 and shaft 12 can be formed integrally. In examples where a screw membrane attachment 38 is used, a silicone cover may be positioned over membrane attachment 38.

Membrane 14 is resiliently flexible. Membrane 14 is movable between at least a first collapsed state (shown in FIG. 1C) and the deployed state shown in FIGS. 1A and 1B. In the first collapsed state, membrane 14 is flexed to move the peripheral portion 36 axially towards the second end portion 24 and radially inwardly towards the shaft axis 20 as indicated by arrow A1 in Figure lC. The membrane 14 may flex to the first collapsed state for inserting the blood flow blocking membrane 14 through a wound.

Referring to FIGS. 1A and 1B, in the deployed state, relative to the first collapsed state, the peripheral portion 36 is moved away from the second end portion 24 and radially outwardly, as indicated by arrow A2 in FIG. 1B. When in the deployed state, membrane 14 can be used for blocking blood flow through the wound. When membrane 14 is positioned in the heart, the deployed state allows the membrane 14 to cover the wound from the interior of the heart.

In some examples, membrane 14 is biased towards the deployed state. In such examples, membrane 14 may flex to the first collapsed state as the membrane passes through a wound (e.g. in a heart) and then automatically return to the deployed state when it has passed through the wound. This allows the membrane 14 to be easily and rapidly positioned to cover the wound on the interior of the heart chamber to block the flow of blood through the wound. In the example shown, there is no need to adjust or inflate or otherwise deploy membrane 14 once inserted into the heart, because it returns to the deployed state automatically. This allows membrane 14 can be quickly maneuvered into position to block the flow of blood through the wound.

Figure 4:
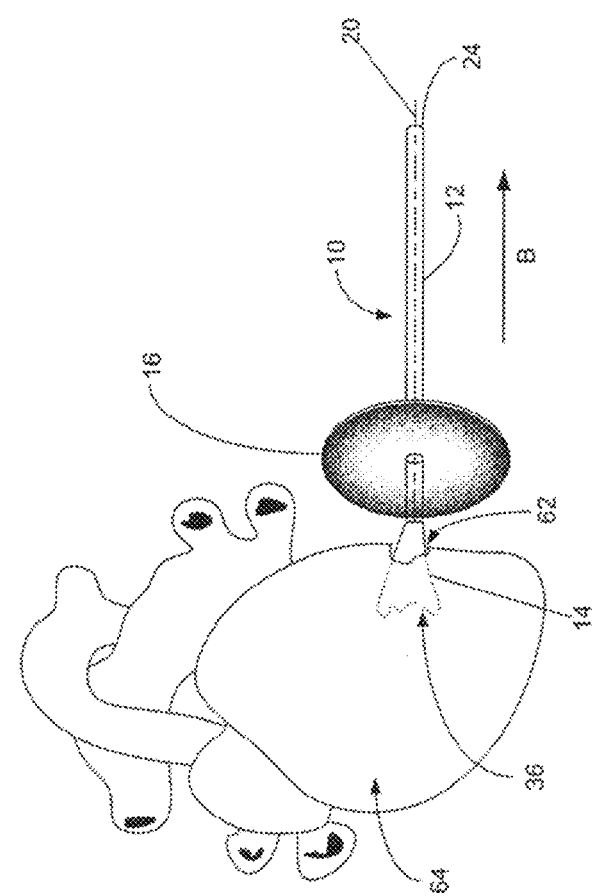
FIG. 4 shows the example device of FIG. 1 being removed from the wound of FIG. 2A with the blood flow blocking membrane in a second collapsed state.

In some examples, membrane 14 can be further movable to and from a second collapsed state (shown in FIG. 4). In the second collapsed state, relative to the deployed state, membrane 14 is flexed to move the peripheral portion 36 axially away from the second end portion 24 and radially inwardly towards the shaft axis 20. The membrane 14 may flex to the second collapsed state for removing the membrane from the wound.

In various examples of device 10, different dimensions of membrane 14 can be used. Differently sized membranes may be used depending on the patient's anatomy (e.g. the size of a heart) and/or the size of the wound. For example, a smaller membrane can be used if the wound is small. A smaller membrane minimizes the volume of the heart occupied by membrane 14 when inserted into the heart. In other examples, larger membranes can be used to block blood flow through larger wounds.

For example, referring to FIG. 1B membrane 14 can have a diameter 52 of between about 2 cm and about 7 cm. In some examples, membrane 14 may have a diameter 52 of about 3.5 cm.

In some examples, membrane 14 can have a deployed surface area (i.e. the area of the first face 30, the second face 32, and the cylindrical side surface) of between about 6 cm 2 and about 80 cm$^2$. In some examples, membrane 14 can have a deployed surface area that is less than about 80 cm$^2$. In some examples, membrane 14 may have a deployed surface area that is about 20 cm$^2$.

In some examples, membrane 14 can have a wall thickness 50 of between about 0.25 mm and about 1.5 mm. In some examples, membrane 14 may have a wall thickness 50 of about 1 mm.

In some examples, membrane 14 can have a deployed volume of between about 0.08 cm 3 and about 6 cm$^3$. In some examples membrane 14 can have a deployed volume of less than about 6 cm$^3$. In some examples, membrane 14 may have a deployed volume that is about 1 cm$^3$.

The use of membrane 14 allows for device 10 to occupy a small volume, e.g. a small volume in the heart. In some examples, the blood flow blocking membrane 14 takes up no more than 2% of the volume of the heart when in the deployed state. In some examples, the blood flow blocking membrane 14 takes up no more than 1% of the volume of the heart when in the deployed state. Thus, membrane 14 may be able to block blood flow through a wound without significantly reducing the volume available in the heart chamber for circulating blood. Accordingly, device 10 may be able to block the flow of blood from a wound in a heart without significantly interfering with cardiac function, such as cardiac valve function.

In various examples, different materials can be used to fabricate membrane 14 and/or abutment member 16. For example, materials used to fabricate prosthetics to replace damaged arteries can be used. Examples of suitable materials include various polymers such as silicone; expanded polytetrafluoroethylene (ePTFE); polyethylene terephthalate ("Dacron"); polyether-urethane; and polycarbonate-urea-urethane. In further examples, bovine pericardium tissue or porcine pericardium tissue, such as those produced by Vascutek Ltd. and Neovasc Inc. can also be used. In some examples, recombinant human tropoelastin can be used as a coating, in order to reduce thrombogenicity. Combinations of the aforementioned materials may also be used.

In the example shown in FIG. 1, membrane 14 is fabricated from silicone. In particular, membrane 14 is a single ply silicone disk. This may facilitate manufacturing of membrane 14 and provide a membrane 14 that occupies a small volume, e.g. a small volume in the patient's heart. As a result, device 10 may be able to block the flow of blood from a wound in a heart without significantly interfering with cardiac function, such as cardiac valve function.

Abutment member 16 is mounted to shaft 12. Abutment member 16 is axially movable along shaft 12 towards and away from the blood flow blocking membrane 14. When membrane 14 is positioned to cover the wound (e.g. the wound inside the heart), abutment member 16 is outside the heart and can be moved axially along the shaft to contact the outside surface of the heart. Abutment member 16 can be used to abut the heart and hold or maintain the blood flow blocking membrane 14 adjacent the wound, so that the device 10 is not drawn further into the heart.

In the example shown in FIG. 1, abutment member 16 has a central bore 42 extending therethrough. Shaft 12 is received in the bore and abutment member 16 is axially slidable along shaft 12. In some examples, abutment member 16 may include a grip 44. Grip 44 can be used to grasp abutment member 16 and move abutment member 16 to the desired axial position on shaft 12.

In alternative examples, the shaft 12 may be threaded, and abutment member may be moved along the shaft by rotating the abutment member 16.

In some examples, abutment member 16 may include an abutment securing member. The abutment securing member can be used to releasably secure the abutment member 16 at the desired axial position on shaft 12. For instance, when the abutment member 16 is positioned to abut the heart, an abutment securing member such as a clip or fastener can be used to secure abutment member 16 in place. For example, a clip can be used to secure abutment member 16 in place along shaft 12.

In some examples, abutment member 16 can be resiliently flexible. This may allow abutment member 16 to conform to the contour of the patient's anatomy, e.g. the heart when abutting the heart. Abutment member 16 may have an abutment member stiffness that is greater than the membrane stiffness of membrane 14. This may reduce the possibility of abutment member 16 being accidentally inserted through the wound when being moved to abut the wound, e.g. the wound in the heart.

In the example device 10 shown in FIG. 1, abutment member 16 has a concave side 40 facing the first end portion 22. The concave side 40 of abutment member 16 may provide a suction action (similar to a suction cup) to secure abutment member 16 in place, e.g. to the heart when moved to abut the heart. This can further facilitate maintaining membrane 14 in position covering the heart, as well as provide additional blocking to prevent the flow of blood through the wound in the heart.

In general, various different examples of device 10 can be used to temporarily manage a wound, such as a wound in a heart. In some examples, device 10 may be a single-use device for temporary management of a wound in a heart. In such examples, device 10 may be discarded after being removed from the patient's heart.

In general, device 10 may be sterilizable and can be sterilized before use to reduce the possibility of infection or contamination of the wound. Device 10 can be sterilized using various known sterilization techniques such as those employing SterradO sterilization systems for example.

Figure 2C:
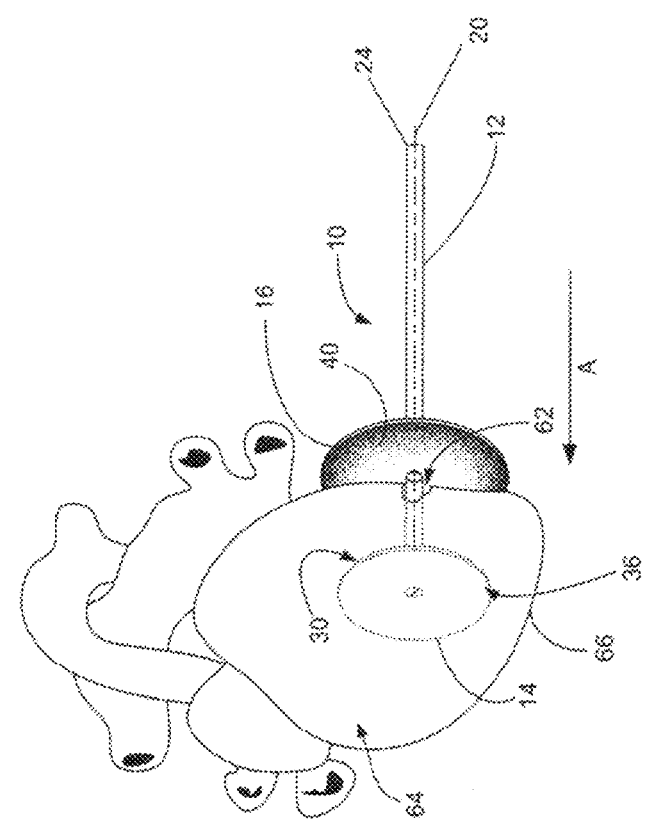
FIG. 2C shows the example device of FIG. 1 after passing through the wound of FIG. 2A with the blood flow blocking membrane in the deployed state.
Figure 3:
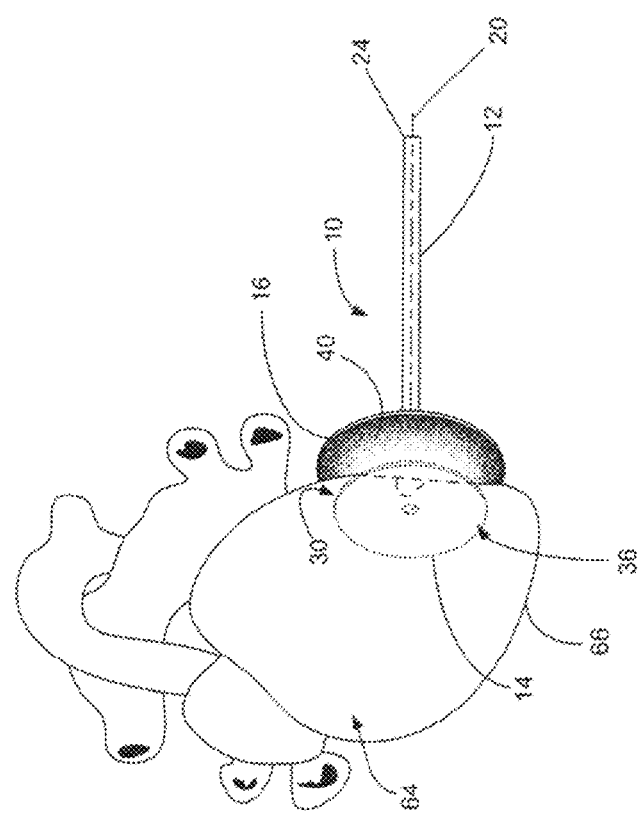
FIG. 3 shows the example device of FIG. 1 with the blood flow blocking membrane positioned to cover the wound of FIG. 2A.

Reference will now be made to FIGS. 2A to 2C, 3, and 4. FIGS. 2B, 3, and 4 show examples of the use of a device for temporary management of a wound in a heart as the device is being inserted through a wound (FIG. 2B), passed through the wound and returned to the deployed state (FIG. 2C), being positioned within the heart to cover the wound (FIG. 3), and being retracted from the wound (FIG. 4). FIG. 2A is an example of a heart 60 with a perforation or wound 62, for example a stab wound. Heart 60 includes a chamber 64 and a wall 66.

Reference is now made to FIG. 2B. FIG. 2B shows heart 60 with the blood flow blocking membrane 14 (and first end portion 22) of device 10 being inserted into wound 62. As the first end portion 22 of device 10 is pushed through wound 62 (in direction A), membrane 14 automatically flexes to the first collapsed state.

In the first collapsed state, the peripheral portion 36 of membrane 14 has moved axially towards the second end portion 24 and radially inwardly towards the shaft axis 20. Contact with heart 60 may cause membrane 14 to flex to the collapsed state. This allows membrane 14 to pass through wound 62 relatively easily, and can minimize the exacerbating effect on the wound of inserting membrane 14.

When the blood flow blocking membrane 14 has passed through wound 62, it can return to the deployed state (shown in FIG. 2C). As mentioned previously, in some examples membrane 14 can be biased to the deployed state. In such examples, membrane 14 automatically returns to the deployed state after passing through wound 62.

Referring now to FIG. 2C, illustrated therein is an example of device 10 with blood flow blocking membrane 14 positioned inside heart 60. Membrane 14 has passed through wound 62 and is now in the deployed state inside chamber 64 of heart 60.

Referring to FIG. 3, once inside heart 60, membrane 14 can be positioned against the wall 66 of the heart 60 to cover wound 62 and block blood flow through wound 62. In some examples, the shaft 12 can be retracted to position the blood flow blocking membrane 14 against the wall 66 of heart 60. A surgeon or surgical assistant can grasp the shaft axis 20 and retract the shaft until membrane 14 is positioned against the inner wall 66 of the heart 60. In some examples, shaft 12 may include a marker on or near first end portion 22 to indicate approximately when shaft 12 has been sufficiently retracted.

Once membrane 14 is positioned against the wall 66, membrane 14 can be maintained against wound 62 to block the flow of blood through wound 62. This can block the flow of blood through wound 62 for an extended period of time, e.g. while a surgeon is performing a procedure in the patient's heart, or while a patient is being transported from an emergency room to an operating room. Although in some examples membrane 14 can be maintained against wound 62 manually, i.e. by a surgeon or surgical assist holding device 10 in place, it may be desirable to maintain membrane 14 in place without requiring the surgeon or other medical professional to hold device 10 in place. This may reduce obstructions in the vicinity of the wound 62 and free the medical professional for other tasks.

Abutment member 16 is usable to maintain membrane 14 against wound 62. After membrane 14 has been positioned against wall 66, abutment member 14 can be moved axially along the shaft towards heart 60 to abut the heart. As mentioned above, the abutment member 16 can be flexible. This may allow abutment member 16 to conform to the contours of heart 60 when abutting the heart 60. As well, abutment member 16 can have a concave side 40 facing membrane 14. The concave side 40 may function as a suction cup to secure abutment member 16 against wall 66 of heart 60 when the abutment member 16 has been moved to abut the heart 60. This may further ensure that membrane 14 is maintained in position against wall 66 covering wound 62.

As mentioned above, abutment member 16 may include an abutment securing member. When abutment member 16 is abutting the heart, the abutment securing member can be secured or fastened to maintain abutment member 16 in the desired axial position on shaft 12. The abutment securing member can subsequently be loosened or released if abutment member 16 needs to be repositioned or when device 10 is being retracted.

In some examples, one or more stitches may be applied to wound 62 while the blood flow blocking membrane 14 is in the heart 60. Because the diameter of membrane 14 is typically much greater than the diameter of shaft 12, the membrane 14 can be used to block the flow of blood through wounds larger than the size of shaft 12. Stitches may be applied to reduce the size of wound 62 before retracting the blood flow blocking membrane 14 from wound 62. Because of the flexible nature of membrane 14, when device 10 is retracted the membrane 14 can be removed from wound 62 even if the size of wound 62 has been reduced because of the stitching. As such, device 10 can be used to rapidly block the bleeding from wound 62 and allow a medical professional to reduce the size of the wound before extracting the device 10.

Referring now to FIG. 4, illustrated therein is an example of device 10 with membrane 14 being retracted from wound 62. Once the device 10 is no longer needed to control the flow of blood through wound 62, the blood flow blocking membrane 14 can be retracted from the wound 62. In FIG. 4, the blood flow blocking membrane 14 is flexed to the second collapsed state as the membrane 14 passes through the wound, moving in direction B.

As shown in FIG. 4, in the second collapsed state, relative to the deployed state of FIGS. 1 and 3, membrane 14 is flexed to move the peripheral portion 36 axially away from the second end portion 24 and radially inward towards the shaft axis 20 to remove the blood flow blocking membrane 14 from the wound. The second collapsed state allows the device 10 to be removed from a patient's heart while minimizes further damage to wound 62. The second collapsed state also facilitates the removal of membrane 14 from heart 60 after stitches have been applied to wound 62.

Figure 7B:
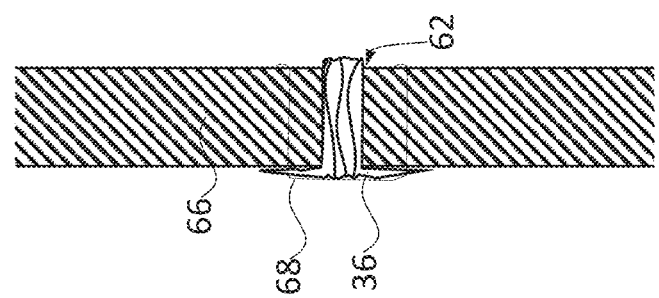
FIG. 7B is a partial cross-section taken through the wall of the heart around the wound, showing the peripheral portion of the blood flow blocking membrane in the wound and stitched to the wall of the heart.
Figure 7A:
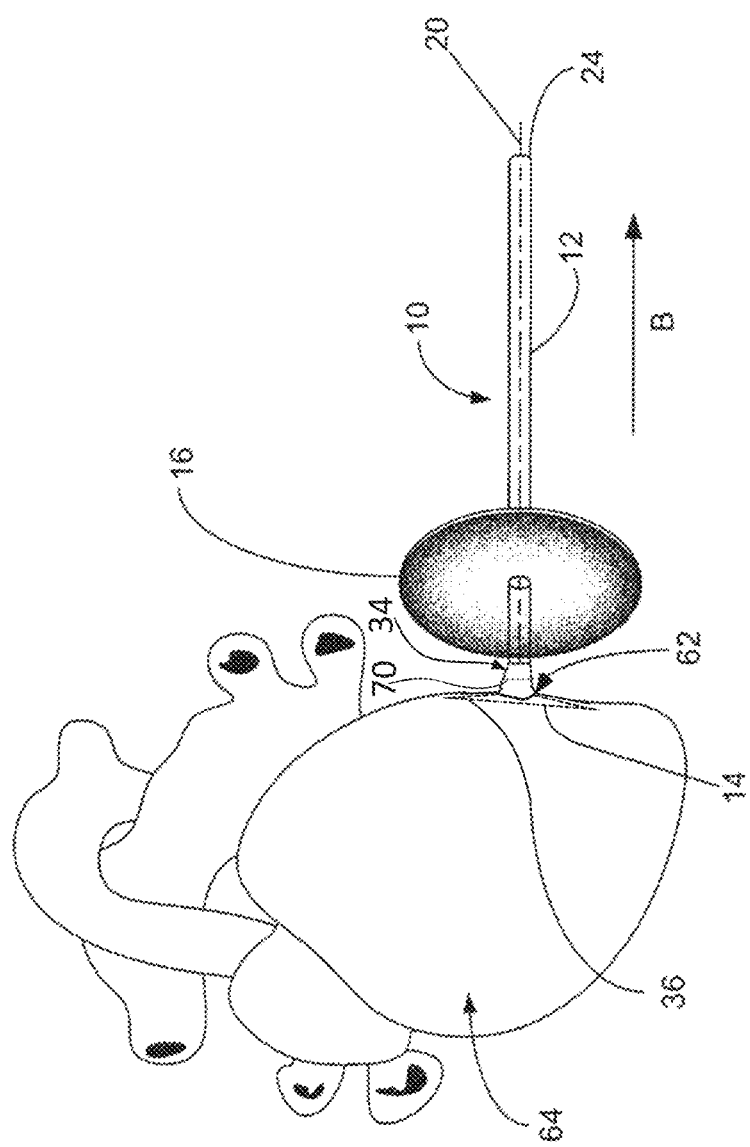
FIG. 7A shows the example device of FIG. 1 being used according to another method, wherein the blood flow blocking membrane has been stitched to the wall of the heart, and wherein the device is being retracted slightly from the wound.

In alternative examples, when applying one or more stitches to the wound, the stitches may be applied through the blood flow blocking membrane 14, to secure a portion of the blood flow blocking membrane 14 to the wall 66 of the heart around the wound 62. The stitches may at first remain loose. Then, as shown in FIG. 7A (wherein for simplicity the stitches are not shown), the device 10 may be retracted slightly, so that the central portion 34 of the blood flow blocking membrane 14 protrudes from the wound 62 a small amount. The central portion 34 of the blood flow blocking membrane 14 may then be separated from the peripheral 36 portion of the blood flow blocking membrane 14, for example by using a scalpel or other cutting tool to sever the peripheral portion 36 of the blood flow blocking membrane 14 from the central portion 34. For example, the blood flow blocking membrane 14 may be cut along line 70 in FIG. 7A. The stitches 68 (shown in FIG. 7B) may be tightened after or concurrently with cutting the blood flow blocking membrane 14. The rest of the device 10 (i.e. the shaft 12, abutment member 16, and central portion 34) may be removed from the patient, leaving the peripheral portion 36 of the blood flow blocking membrane 14 in the wound 62 and occluding the wound 62, as shown in FIG. 7B. The peripheral portion 36 of the blood flow blocking membrane 14 may stay in the heart indefinitely.

EXAMPLES

A device as shown in FIGS. 1A to 1C (referred to hereinafter as "the device" was tested and compared to a urinary balloon catheter (Foley catheter) for the control of bleeding in experimental penetrating cardiac wounds. Currently, a commonly used method to obtain temporary control of bleeding in penetrating cardiac injuries is the insertion of a Foley catheter through the wound, followed by traction to tightly position the balloon against the injury. In practice, this technique can result in suboptimal control of the bleeding and can lead to enlargement of the initial injury. Moreover, the balloon inevitably occupies space inside the cardiac chamber, thereby interfering with cardiac function.

Methods

Six (n=6) adult male Yorkshire pigs (35-37 kg) were fasted overnight before the procedure and were maintained at 25° C. on 12-hour light/dark cycles.

Animals were anesthetized with intramuscular ketamine (20 mg/kg), xylazine (2 mg/kg) and atropine sulphate (1 mg/25 kg, 1-2 mL). Once anesthetized, animals were intubated and maintained on a ventilator (10 ml/kg) with inhaled isoflurane 2-5% for anesthesia maintenance throughout the procedure.

Pulse oximetry, electro cardiogram (ECG), and heart rate were monitored continuously. The right femoral artery of each swine was cannulated with a 14 gauge vascular catheter and mean arterial blood pressure pressure (MAP) was continuously monitored (Biopac Systems Inc., Goleta, Calif.). The right jugular vein was cannulated in similar fashion for fluid infusion. Animals received intravenous lactated Ringer's solution to maintain MAP at baseline levels±5 mmHg throughout the procedure.

Each swine was randomly selected to have either the device or a Foley catheter placed in standardized (1.5 cm) cardiac wounds in the right ventricle (RV) and in the left ventricle (L V). A total of 4 wounds were created in each animal, two in each cardiac chamber. After each wound was created, either the device or the Foley catheter was used to temporarily manage the bleeding.

Two surgical blades were joined together on a scalpel handle to create a consistent wound of 1.5 cm in length. A suction catheter was used for aspiration of blood. A median sternotomy was performed and the pericardial sac opened to expose the heart. Intra-operative echocardiogram was performed prior to creating the wound.

For each swine, the method selected to control bleeding in the first wound was randomly selected. A full thickness 1.5 cm wound was then created along the longitudinal axis of the right ventricle. The wound was allowed to bleed for 5 seconds before temporary hemorrage control was attempted and either the device or the Foley catheter was introduced into the wound (depending on the random selection).

When the device as described herein was used, the device was deployed by inserting the blood flow blocking membrane through the cardiac wound. The blood flow blocking membrane was positioned against an undersurface of the ventricle wall. The abutment member was moved axially along the shaft of the device towards the wound. The blood flow blocking membrane was then maintained against the undersurface of the ventricle wall. The device was then retracted from the wound by sliding the abutment member away from the wound and pulling the device out of the ventricle through the cardiac wound.

When the Foley catheter was used, the Foley catheter was introduced into the ventricle through the wound and the balloon insuflated with 10 ml of normal saline. The Foley catheter was removed by deflating the balloon and pulling the catheter out of the ventricle through the wound.

All bleeding was aspirated and the volume ascertained.

Another echocardiogram was performed after complete control of the bleeding. The wound was sutured using 3-0 polypropylene sutures.

Figure 5:
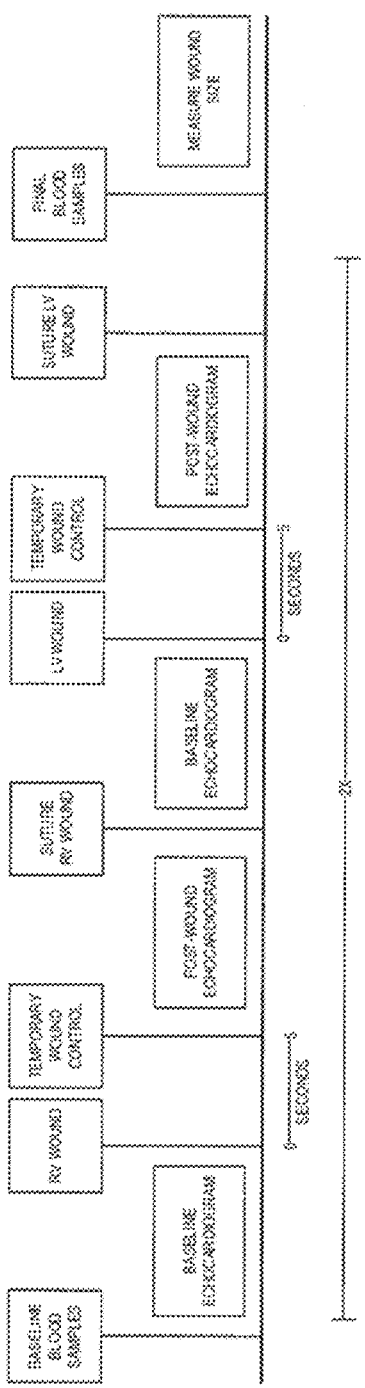
FIG. 5 shows a timeline of the experimental methodology used in a study to compare wound management results achieved with the example device of FIG. 1 with a Foley catheter.

Ringer's lactate solution was infused in boluses to maintain MAP at baseline levels±5 mmHg. Once that pressure was achieved, and the animal became stable for 5 minutes, another echocardiogram was performed. Thereafter, a new wound was created in the left ventricle in the manner previously described. Hemorrhage control and all other procedures were the same as described for the right ventricular wound. The aforementioned methodology was repeated alternately using the example device and the Foley catheter twice in each animal. FIG. 5 shows a timeline of the methodology employed.

After all four wound interventions were complete, the animals were euthanized with the injection of T-61 euthanasia solution (Merck Animal Health Intervet Canada Corp. Kirkland, QC). The sutures were subsequently removed and the size of each wound was measured.

Arterial blood samples were obtained at baseline and at the end of the experiment to measure arterial blood gases (ABG), complete blood count (CBC), coagulation profile, troponin, fibrinogen, and serum lactate. Intra-operative echocardiograms were performed before insertion and while the example device or the Foley catheter was in place.

The Student's t test was used to analyze comparisons between the two methods, with $p<0.05$ being considered statistically significant. Hemodynamic and laboratory data are shown as the mean±SD. Echocardiographic data is shown as a percent change from baseline values.

Results

The mean weight of the animals was 36.1±0.3 Kg. There was a significant decrease ($p<0.05$) in final CBC values compared to baseline. Bleeding from the cardiac wounds resulted in a significant ($p<0.05$) decrease in the red blood cell count RBC: 5.3±0.3 vs. 3.9±0.3×10 12/L, hemoglobin levels Hgb: 91±4.8 vs. 66.5±4.5 g/dL, and hematocrit HCT: 0.3±0.01 vs.0.2±0.02 L/L.

Platelet count and fibrinogen levels reduced significantly; respectively, PLT: 271 0.5±30.9 vs. 223.2±16.1×10 9/L, $p<0.05$ and fibrinogen 1.6±0.2 vs. 1.1±0.1 g/dL, $p<0.05$. Prothrombin time and activated prothrombin time increased compared to baseline; respectively, PT: 14.6±0.4 vs. 15.9±0.3 seconds, $p<0.05$ and APTT: 10.6±0.4 vs. 12.18±0.2 seconds, $p<0.05$.

Bleeding also resulted in shock as demonstrated by the significant increase in the serum lactate levels compared to baseline, 2.6±0.3 vs. 4.8±0.9 mmol/L, $p<0.05$. Bleeding from the cardiac wounds significantly increased serum lactated levels compared to baseline; respectively 2.6±0.3 vs. 4.8±0.9 mmol/L, $p<0.05$. There were no statistically significant differences in ABG values between baseline and final samples. Troponin levels increased after the wounds compared to baseline; respectively 0.2±0.005 vs. 0.9±0.07 ng/ml, $p<0.05$.

Figure 6A:
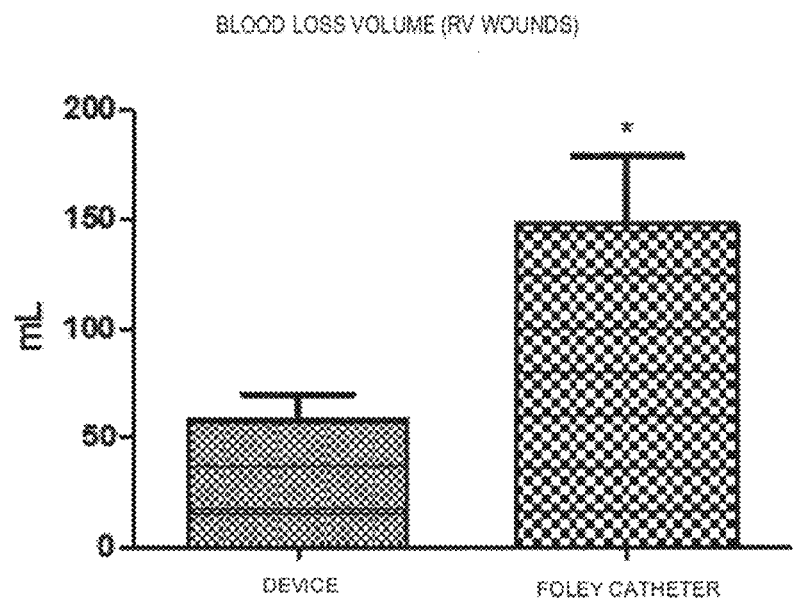
FIG. 6A shows a plot of blood loss volume from right ventricle wounds when using the example device of FIG. 1 for temporary wound management compared with using a Foley catheter.

FIG. 6A shows a plot of the blood loss volume from the RV wounds when the device was used and when the Foley catheter was used. FIG. 6A shows that bleeding from the RV wounds (58.7±11.3 ml) was significantly less when the device was used as compared to the Foley catheter (147.7±30.9 ml) with $p<0.05$.

Figure 6B:
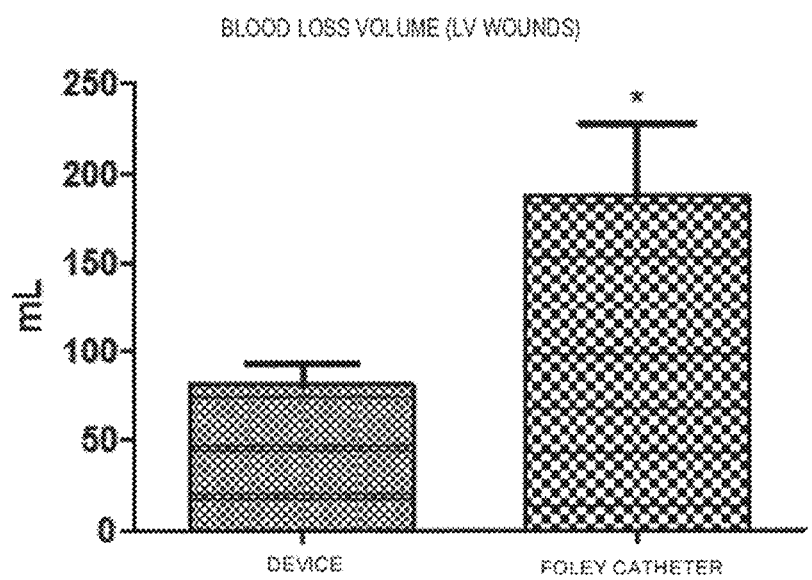
FIG. 6B shows a plot of blood loss volume from left ventricle wounds when using the example device of FIG. 1 for temporary wound management compared with using a Foley catheter.

FIG. 6B shows a plot of the blood loss volume from the LV wounds when the device was used and when the Foley catheter was used. As FIG. 6B shows, bleeding from the LV wounds was also significantly less with the example device (81.7±11.9 ml) compared to the Foley catheter (187.5±40.3 ml) with $p<0.05$.

Figure 6C:
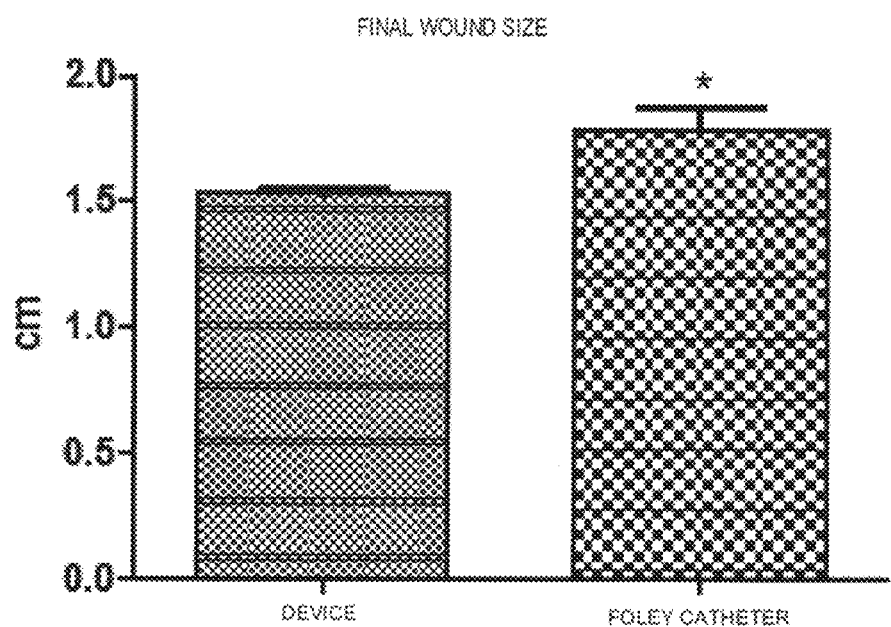
FIG. 6C shows a plot of final wound size when using the example device of FIG. 1 for temporary wound management compared with using a Foley catheter.

FIG. 6C shows a plot of the final lengths of the cardiac wounds when the device was used and when the Foley catheter was used. FIG. 6C shows that the final lengths of the cardiac wounds were significantly longer when the Foley catheter was used (1.8±0.1 cm) to control bleeding as compared to the device (1.53±0.02 cm) with p<0.05.

Echocardiographic data was assessed separately for the first and second sets of wounds. The following parameters were analyzed:
  Tricuspid regurgitation (T R)
  Mitral regurgitation (MR)
  Right ventricular fractional area change (RVFAC)
  Stroke volume (SV)
  Left ventricular ejection fraction (LVEF)

The intra-operative echocardiogram data also showed that the device outperformed the Foley catheter in 4 out of 5 measurements based on percent change compared to baseline.

The percent changes compared to baseline for MR were 100% increase with the example device vs. 51.5% increase with the Foley catheter. Assessment of the percent changes of the other echocardiogram parameters listed above, were consistently lower with the insertion of the example device compared to the insertion of the Foley catheter: TR (66.6% increase with the device vs. 400% increase with the Foley catheter); RVFAC (6.62% decrease with the example device vs. 21.76% decrease with the Foley catheter); SV (2.09% decrease with the example device vs. 12.48% decrease with the Foley catheter); and LVEF (0.46% decrease with the device vs. 5.45% decrease with the Foley catheter).

Similarly, when the device or the Foley catheter were used in the setting of a previously repaired cardiac wound, the percent changes compared to baseline for TR were 203% increase with the insertion of the device vs. 83% increase with the insertion of the Foley catheter. The percent changes of the other parameters, in the setting of a previous wound, were consistently lower with the insertion of the example device compared to the insertion of the Foley catheter. Namely, MR (no change with the example device vs. 16% increase with the Foley catheter), RVFAC (3.9% increase with the example device vs. 7.8% increase with the Foley catheter), SV (5.25% decrease with the example device vs. 13.53% decrease with the Foley catheter), and LVEF (5.78% decrease with the example device vs. 8.03% decrease with the Foley catheter).

The study results indicate that the device can effectively control bleeding and may outperform the Foley catheter in several aspects. In the study, the insertion of the example device through the injury resulted in significantly less bleeding than with the insertion of the Foley catheter.

The device also did not require traction or balloon insufflation to control bleeding. In contrast, an inflated balloon unavoidably occupies space inside the ventricle that otherwise would be filled with blood. This may also lead to blood flow obstruction. This may interfere with cardiac function, which is particularly undesirable for patients who present with penetrating cardiac injuries. The study results also showed fewer changes in echocardiogram parameters with the example device than the Foley catheter, notably in stroke volume and left ventricular ejection fraction.

The example device occluded the cardiac wound through a combination of downward pressure on the outer surface of the heart by the abutment member balanced against an upward pressure on the inner surface of the ventricle produced by the blood flow blocking membrane. In contrast, wound occlusion with the Foley catheter was obtained by upward traction only, thereby creating pressure against the inner surface of the ventricle. In the event that an excessive traction is applied on the catheter to control bleeding, the pressure exerted by the balloon against the inner surface of the ventricle can potentially enlarge the wound. This may explain the significant increase in the size of the wounds following the use of the Foley catheter in this study.

The blood flow blocking membrane of the device also maintained continuous control of the bleeding as it was being removed from the ventricles. This facilitated proper placement of the sutures during the definitive repair. On the other hand, deflating the balloon during removal of the Foley catheter frequently led to bleeding from the wound. Moreover, attempts to suture repair the wound without deflating the balloon frequently resulted in damage to the balloon and bleeding.

The new device provided efficient temporary control of bleeding in penetrating cardiac injuries to the ventricles. Moreover, the device outperformed the Foley catheter in both hemorrhage control and interference with cardiac function.

While the above description provides examples of one or more processes or apparatuses, it will be appreciated that other processes or apparatuses may be within the scope of the accompanying claims.

I claim:

1. A method for temporary management of a wound in a heart, the method comprising:
   a. inserting a blood flow blocking membrane through the wound, wherein the blood flow blocking membrane is at a first end portion of a shaft, the blood flow blocking membrane flexing to a first collapsed state as the blood flow blocking membrane passes through the wound, and returning to a deployed state when it has passed through the wound;
   b. positioning the blood flow blocking membrane against a wall of the heart to cover the wound and to block blood flow through the wound;
   c. maintaining the blood flow blocking membrane against the wound; and
   d. applying a stitch to the wall of the heart to stitch a portion of the blood flow blocking membrane to the wall of the heart, and separating the portion of the blood flow blocking membrane from the shaft.

2. The method of claim 1, wherein the blood flow blocking membrane takes up no more than 1% of the volume of the heart when in the deployed state.

3. The method of claim 1, wherein
   step a. comprises inserting the first end portion of the shaft into the wound
   step b. comprises retracting the shaft to position the blood flow blocking membrane against the wall of the heart; and
   step c. comprises moving an abutment member axially along the shaft towards the heart to contact the heart.

4. The method of claim 3, further comprising retracting the shaft and the abutment member from the wound.

5. The method of claim 1, wherein in step a., contact with the heart causes the blood flow blocking membrane to flex to the collapsed state, and the blood flow blocking membrane automatically returns to the deployed state after passing through the wound.

6. A method for temporary management of a wound in a heart, the method comprising:
   a. inserting a blood flow blocking membrane through the wound, the blood flow blocking membrane flexing to a first collapsed state as the blood flow blocking membrane passes through the wound, and returning to a deployed state when it has passed through the wound;

b. positioning the blood flow blocking membrane against a wall of the heart to cover the wound and to block blood flow through the wound;
c. maintaining the blood flow blocking membrane against the wound; and
d. applying a stitch to the wound while the blood flow blocking membrane is in the heart, and retracting the blood flow blocking membrane from the wound, the blood flow blocking membrane flexing to a second collapsed state as the blood flow blocking membrane passes through the wound.

7. The method of claim 6, wherein the blood flow blocking membrane takes up no more than 1% of the volume of the heart when in the deployed state.

8. The method of claim 6, wherein
step a. comprises inserting a first end portion of a shaft into the wound, wherein the blood flow blocking membrane is at the first end portion of the shaft;
step b. comprises retracting the shaft to position the blood flow blocking membrane against the wall of the heart; and
step c. comprises moving an abutment member axially along the shaft towards the heart to contact the heart.

9. The method of claim 8, further comprising retracting the shaft and the abutment member from the wound.

10. The method of claim 6, wherein in step a., contact with the heart causes the blood flow blocking membrane to flex to the collapsed state, and the blood flow blocking membrane automatically returns to the deployed state after passing through the wound.

* * * * *